US005811510A

United States Patent [19]
Papisov

[11] Patent Number: 5,811,510
[45] Date of Patent: Sep. 22, 1998

[54] BIODEGRADABLE POLYACETAL POLYMERS AND METHODS FOR THEIR FORMATION AND USE

[75] Inventor: Mikhail I. Papisov, Winchester, Mass.

[73] Assignee: General Hospital Corporation, Boston, Mass.

[21] Appl. No.: 421,766

[22] Filed: Apr. 14, 1995

[51] Int. Cl.[6] .................................................. C08G 4/00
[52] U.S. Cl. .................. 528/230; 528/230; 528/232; 528/239; 525/400; 525/401; 525/403; 525/405; 525/417; 514/693; 514/696; 424/78.08
[58] Field of Search ................................ 528/230, 232, 528/239; 525/400, 401, 403, 405, 417; 514/693, 696; 424/78.08

[56] References Cited

U.S. PATENT DOCUMENTS

| | | | |
|---|---|---|---|
| 4,024,073 | 5/1977 | Shimizu et al. | 252/316 |
| 5,202,434 | 4/1993 | Wilkening | 540/454 |
| 5,359,071 | 10/1994 | Durette et al. | 546/78 |
| 5,460,752 | 10/1995 | Fredj t al. | 252/542 |

FOREIGN PATENT DOCUMENTS

| | | |
|---|---|---|
| 0 113 123 | 7/1984 | European Pat. Off. . |
| 0 280 474 | 8/1988 | European Pat. Off. . |
| 0 304 183 | 2/1989 | European Pat. Off. . |
| 0 584 034 | 2/1994 | European Pat. Off. . |

*Primary Examiner*—Samuel A. Acquah
*Attorney, Agent, or Firm*—Hamilton, Brook, Smith & Reynolds, P.C.

[57] ABSTRACT

The present invention relates to biodegradable biocompatible polyacetals, methods for their preparation, and methods for treating mammals by administration of biodegradable biocompatible polyacetals. A method for forming the biodegradable biocompatible polyacetals combines a glycol-specific oxidizing agent with a polysaccharide to form an aldehyde intermediate which is combined with a reducing agent to form the biodegradable biocompatible polyacetal. The resultant biodegradable biocompatible polyacetals can be chemically modified to incorporate additional hydrophilic moieties. A method for treating mammals includes the administration of the biodegradable biocompatible polyacetal in which biologically active compounds or diagnostic labels can be disposed.

30 Claims, 1 Drawing Sheet

BIODEGRADABLE POLYACETAL POLYMERS AND METHODS FOR THEIR FORMATION AND USE

BACKGROUND OF THE INVENTION

Polymers which are degraded by a physical or chemical process in response to contact with body fluid, while implanted or injected, are generally considered to be biodegradable. Biodegradable polymers have been the subject of increasing interest as materials which can be employed to form a wide variety of pharmaceutical preparations and other biomedical products. Examples of medical applications for biodegradable polymers include tablet coatings, plasma substitutes, gels, contact lenses, surgical implants, systems for controlled drug release, as ingredients of eyedrops, and as long circulating and targeted drugs.

Many polymers have hydrophobic domains and, consequently, their biocompatability is limited. Hydrophobic polymers are vulnerable to non-specific interactions with proteins and lipids which also may cause undesirable side effects. In addition, synthetic polymers, such as vinyl, acrylic and methacrylic polymers, which typically have a hydrophobic main chain that do not degrade readily in vivo.

Hydrophilic polymers are common in nature. For example, polysaccharides are naturally-occurring polymers which include hydrolytically-sensitive acetals in their main chain. However, polysaccharides can interact with cell receptors and/or plasma opsonins, which can cause adverse reactions and other non-desirable effects.

Polyacetals can be formed synthetically. However, most synthetic polyacetals contain acetal group not in the main chain. Further, known synthetic polyacetals with acetal groups in the main chain are essentially hydrophobic and have limited solubility in water. They also do not include pharmaceutical substituents.

Therefore, a need exists for a polymer which overcomes or minimizes the above-referenced problems.

SUMMARY OF THE INVENTION

The present invention relates to biodegradable polyacetals, methods for their preparation, and methods for treating and studying mammals by administration of biodegradable polyacetals.

Biodegradable biocompatible polyacetals of the present invention have the following chemical structure:

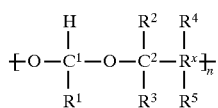

$R^1$ is a biocompatible group and includes a carbon atom covalently attached to $C^1$. $R^x$ includes a carbon atom covalently attached to $C^2$. "n" is an integer. $R^2$, $R^3$, $R^4$ and $R^5$ are biocompatible groups and are selected from the group consisting of hydrogen and organic moieties. At least one of $R^1$, $R^2$, $R^3$, $R^4$ and $R^5$ is hydrophilic.

One method for forming a biodegradable polyacetal of the invention includes combining a molar excess of a glycol-specific oxidizing agent with a polysaccharide to form an aldehyde intermediate. The aldehyde intermediate is then reacted to form the biodegradable polyacetal.

A second method for forming biodegradable polyacetals includes combining a cationic initiator with a reactant having the chemical structure:

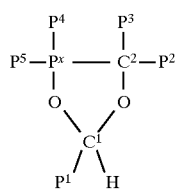

The reactant is converted to a polymer having the chemical structure:

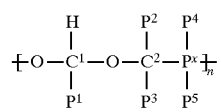

$P^1$ is a protected hydrophilic group which includes a carbon atom covalently attached to $C^1$. $P^x$ is a protected hydrophilic group which includes a carbon atom covalently attached to $C^2$. "n" is an integer. At least one of $P^1$, $P^2$, $P^3$, $P^4$ and $p^5$ is selected from hydrogen and protected hydrophilic groups.

The method for treating a mammal comprises administering the biodegradable biocompatible polyacetal to the mammal. Pharmaceutical excipients, such as biologically active compounds or diagnostic labels, can be incorporated into a solution or a gel which includes the biodegradable biocompatible polyacetal of the invention. Mixtures of pharmaceutical excipients can be disposed within the solution or gel. For example, pharmaceutical excipients can be linked to the polyacetal by a chemical bond or dispersed throughout the biocompatible biodegradable polyacetal solution or gel.

This invention has many advantages. For example, the reactants employed to form the biodegradable biocompatible polyacetals are readily available. Further, the resultant biodegradable biocompatible polyacetals can be modified to obtain products with desirable properties, such as by modification with additional hydrophilic moieties, biologically active groups, or diagnostic groups. Also, the biodegradable biocompatible polyacetal can incorporate pharmaceutical excipients. The biodegradable biocompatible polyacetals can be formed to meet narrow requirements of biodegradability and hydrophilicity. The biodegradable biocompatible polyacetals of the present invention are distinct from naturally-occurring polysaccharides. For example, the polysaccharide ring structure is cleaved during the synthesis of the biodegradable biocompatible polyacetals and is essentially absent from the polymer structure. Further, the biodegradable biocompatible polyacetals of the present invention have a higher degree of biocompatability relative to the polysaccharides from which they are derived, since they generally do not contain cyclic carbohydrates-which are potentially receptor recognizable.

DETAILED DESCRIPTION OF THE INVENTION

Figure 1:
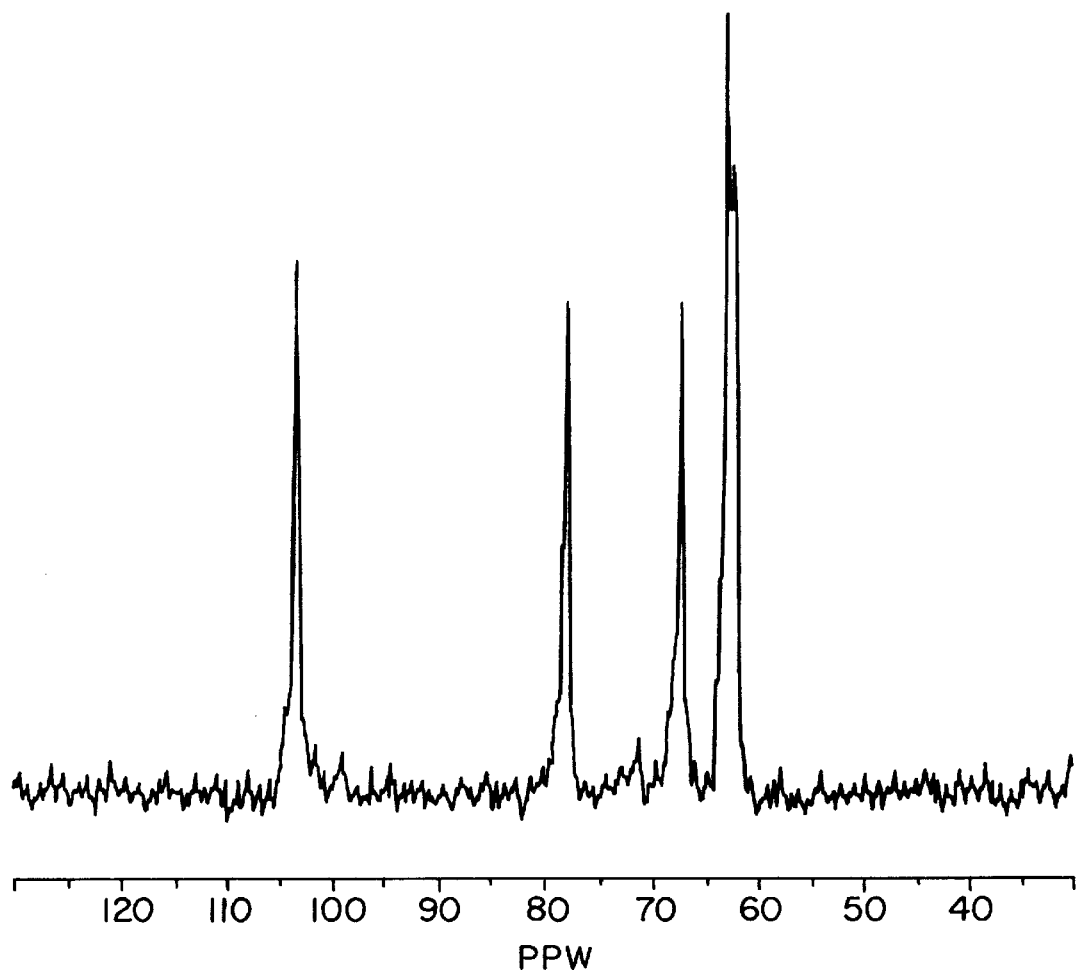
FIG. 1 is a $^{13}C$ NMR spectrum of a biodegradable biocompatible polyacetal of the present invention.

The features and other details of the invention, either as steps of the invention or as combination of parts of the invention, will now be more particularly described and pointed out in the claims. It will be understood that the particular embodiments of the invention are shown by way of illustration and not as limitations of the invention. The principle features of the invention may be employed in various embodiments without departing from the scope of the invention.

The biodegradable biocompatible polyacetals of the present invention are hydrophilic, hydrolyzable, contain acetal groups in the main chain and can be functionalized. Solubility of biodegradable biocompatible polyacetals can be modified by subsequent substitution of additional hydrophilic or hydrophobic groups. Biodegradable biocompatible polyacetals of the present invention can be employed as components of biomaterials, pharmaceutical formulations, medical devices, implants, and can be combined with biologically active compounds and diagnostic labels.

"Biodegradable," as that term is used herein, means polymers which are degraded in response to contact with body fluid while implanted or injected in vivo. Examples of biodegradation processes include hydrolysis, enzymatic action, oxidation and reduction. Suitable conditions for hydrolysis, for example, include exposure of the biodegradable polyacetals to water at a temperature and a pH of circulating blood. Biodegradation of polyacetals of the present invention can be enhanced in low pH regions of the mammalian body, e.g. an inflamed area. "Biocompatible," as that term is used herein, means exhibition of essentially no cytotoxicity while in contact with body fluids. "Biocompatibility" also includes essentially no interactions with recognition proteins, e.g., naturally occurring antibodies, cell proteins, cells and other components of biological systems. However, substances and functional groups specifically intended to cause the above effects, e.g., drugs and prodrugs, are considered to be biocompatible.

The biodegradable biocompatible polyacetals of the present invention have the following chemical structure:

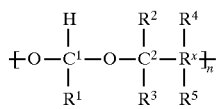

$R^1$ is biocompatible and includes a carbon atom covalently attached to $C^1$. $R^x$ includes a carbon atom covalently attached to $C^2$. "n" is an integer. $R^2$, $R^3$, $R^4$ and $R^5$ are biocompatible and are selected from the group consisting of hydrogen and organic moieties. At least one of $R^1$, $R^2$, $R^3$, $R^4$ and $R^5$ is hydrophilic. Examples of suitable organic moieties are aliphatic groups having a chain of atoms in a range of between about one and twelve atoms.

The term "hydrophilic" as it relates to $R^1$, $R^2$, $R^3$, $R^4$ and $R^5$ denotes organic moieties which contain ionizable, polar, or polarizable atoms, or which otherwise may bind water molecules. Examples of particular hydrophilic organic moieties which are suitable include carbamates, amides, hydroxyls, carboxylic acids and their salts, carboxylic acid esters, amines, sulfonic acids and their salts, sulfonic acid esters, phosphoric acids and their salts, phosphate esters, polyglycol ethers, polyamines, polycarboxylates, polyesters, polythioethers, etc. In preferred embodiments of the present invention, at least one of $R^1$, $R^2$, $R^3$, $R^4$ and $R^5$ include a carboxyl group (COOH), an aldehyde group (CHO) or a methylol (CH$_2$OH). In another preferred embodiment of the present invention, $R^1$, $R^2$, $R^3$, $R^4$ and $R^5$ are methylols. In still another preferred embodiment of the present invention, $R^1$ and $R^2$ are methylols and $R^3$, $R^4$, and $R^5$ are hydrogens.

In yet another embodiment of the present invention, at least one of $R^1$, $R^2$, $R^3$, $R^4$ or $R^5$ is a nitrogen-containing compound. The nitrogen-containing compound can be a drug or a crosslinking agent or a functional group which is suitable as a modifier of biodegradable biocompatible polyacetal behavior in vivo. Examples of such functional groups include antibodies, their fragments, receptor ligands and other compounds that selectively interact with biological systems.

Alternatively, the nitrogen-containing compound can have a chemical structure of –$C_nH_{2n}NR^6R^7$, wherein "n" is an integer. In one embodiment, "n" is one. $R^6$ and $R^7$ can include hydrogen, organic or inorganic substituents. Examples of suitable organic or inorganic groups include aliphatic groups, aromatic groups, complexes of heavy metals, etc.

The biodegradable biocompatible polyacetals of the invention can be crosslinked. A suitable crosslinking agent has the formula $X^1$—(R)—$X^2$, where R is a spacer group and $X^1$ and $X^2$ are reactive groups. Examples of suitable spacer groups include biodegradable or nonbiodegradable groups, for example, aliphatic groups, carbon chains containing biodegradable inserts such as disulfides, esters, etc. The term "reactive group," as it relates to $X^1$ and $X^2$, means functional groups which can be connected by a reaction within the biodegradable biocompatible polyacetals, thereby crosslinking the biodegradable biocompatible polyacetals. Suitable reactive groups which form crosslinked networks with the biodegradable biocompatible polyacetals include epoxides, halides, tosylates, mesylates, carboxylates, aziridines, cyclopropanes, esters, N-oxysuccinimde esters, disulfides, anhydrides etc.

In one of the preferred embodiments of the present invention, the biodegradable biocompatible polyacetals are crosslinked with epibromohydrin or epichlorohydrin. More preferably, the epibromohydrin or epichlorohydrin is present in an amount in the range of between about one and twenty five percent by weight of the crosslinked biodegradable biocompatible polyacetals.

Alternatively, the term "reactive" group as it relates to $X^1$ and $X^2$ means a nucleophilic group that can be reacted with an aldehyde intermediate of the biodegradable biocompatible polyacetals, thereby crosslinking the biodegradable biocompatible polyacetals. Suitable reactive groups for the aldehyde intermediate include amines, thiols, polyols, alcohols, ketones, aldehydes, diazocompounds, boron derivatives, ylides, isonitriles, hydrazines and their derivatives and hydroxylamines and their derivatives, etc.

In one embodiment, the biodegradable biocompatible polyacetals of the present invention have a molecular weight of between about 0.5 and 500 kDa. In a preferred embodiment of the present invention, the biodegradable biocompatible polyacetals have a molecular weight of between about 1 and 100 kDa.

At least one of $R^1$, $R^2$, $R^3$, $R^4$ and $R^5$ can comprise a biologically-active compound, such as a drug molecule. Examples of suitable drug molecules comprise a biologically active functional group fragment or moiety, or a diagnostic label. Specific examples of suitable drug molecules include antibiotics, analgesics, amino acids, vitamins, and chemotherapeutic agents. Examples of biologically active compounds are chemotherapeutic agents, antibacterial agents, antiviral agents, immunomodulators, hormones and their analogs, enzymes, inhibitors, alkaloids, therapeutic radionuclides, etc. Suitable chemotherapeutic compounds are, for example, alkylating agents, anthracyclines, doxorubicin, cisplatin, carboplatin, vincristine, mitromycine, dactinomycines, etc. Other suitable compounds include therapeutic radionuclides, such as β-emitting isotopes of rhenium, cesium, iodine, and alkaloids, etc. In one embodiment of the present invention, at least one of $R^1$, $R^2$, $R^3$, $R^4$ and $R^5$ contains doxorubicin.

In another embodiment of the present invention, at least one of $R^1$, $R^2$, $R^3$, $R^4$ and $R^5$ comprises a diagnostic label. Examples of suitable diagnostic labels include diagnostic radiopharmaceuticals, contrast agents for magnetic resonance imaging, contrast agents for computed tomography and other methods of X-ray imaging and agents for ultrasound diagnostic methods, etc. Diagnostic radiopharmaceuticals include γ-emitting radionuclides, e.g., indium-111, technetium-99m.and iodine-131, etc. Contrast agents for MRI (Magnetic Resonance Imaging) include magnetic compounds, e.g. paramagnetic ions, iron, manganese, gadolinium, lanthanides, organic paramagnetic moieties and superparamagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron. Further, substituents can be employed which can reflect, scatter, or otherwise affect X-rays, ultrasound, radiowaves, microwaves and other rays useful in diagnostic procedures. In a preferred embodiment, at least one of $R^1$, $R^2$ and $R^3$ comprises a paramagnetic ion or group.

Optionally, the invention can be a composition in the form of a gel of the biodegradable biocompatible acetal and a biologically active compound disposed within the gel. Alternatively or additionally, a diagnostic label can be disposed within the gel.

In another embodiment, the invention can be a composition in the form of a solution of the biodegradable biocompatible acetal and a biologically active compound dissolved within the solution. Alternatively, a diagnostic label can be dissolved within the solution.

In one embodiment of the method for forming the biodegradable biocompatible polyacetal of the present invention, a suitable polysaccharide is combined with a molar excess of a glycol-specific oxidizing agent to form an aldehyde intermediate. A "molar excess of a glycol-specific oxidizing agent," as that phrase is employed herein, means an amount of the glycol-specific oxidizing agent that provides oxidative opening of essentially all carbohydrate rings of the polysaccharide. The aldehyde intermediate is then combined with a reducing-agent to form the biodegradable biocompatible polyacetal. The biodegradable biocompatible polyacetals of the present invention can form linear or branched structures. The biodegradable biocompatible polyacetal of the present invention can be optically active. Optionally, the biodegradable biocompatible polyacetal of the present invention can be racemic.

Structure, yield and molecular weight of the resultant polyaldehyde depend on the initial polysaccharide. Polysaccharides that do not undergo significant depolymerization in the presence of glycol-specific oxidizing agents, for example, poly (1→6) hexoses, are preferable. Examples of suitable polysaccharides include starch, cellulose, dextran, etc. A particularly preferred polysaccharide is dextran. Examples of suitable glycol-specific oxidizing agents include sodium periodate, lead tetra-acetate, etc. Examples of suitable reducing agents include sodium borohydride, sodium cyanoborohydride, etc.

In an embodiment wherein dextran is employed as a reactant to form the biodegradable biocompatible polyacetal, the glycol-specific oxidation can be conducted at a temperature between about 25° C. and 40° C. for a period of about eight hours at a suitable pH. Temperature, pH and reaction duration can affect the reaction rate and polymer hydrolysis rate. The reaction is preferably conducted in the absence of light. One skilled in the art can optimize the reaction conditions to obtain polymers of desired composition. The resultant aldehyde intermediate can be isolated and combined with a solution of a reducing agent for a period of about two hours to form the biodegradable biocompatible polyacetal after isolation. Alternatively, aldehyde groups can be conjugated with a variety of compounds or converted to other types of functional groups.

It is believed that the carbohydrate rings of a suitable polysaccharide can be oxidized by glycol-specific reagents with cleavage of carbon bonds between carbon atoms that are connected to hydroxyl groups. The following mechanism is an example of what is believed to occur.

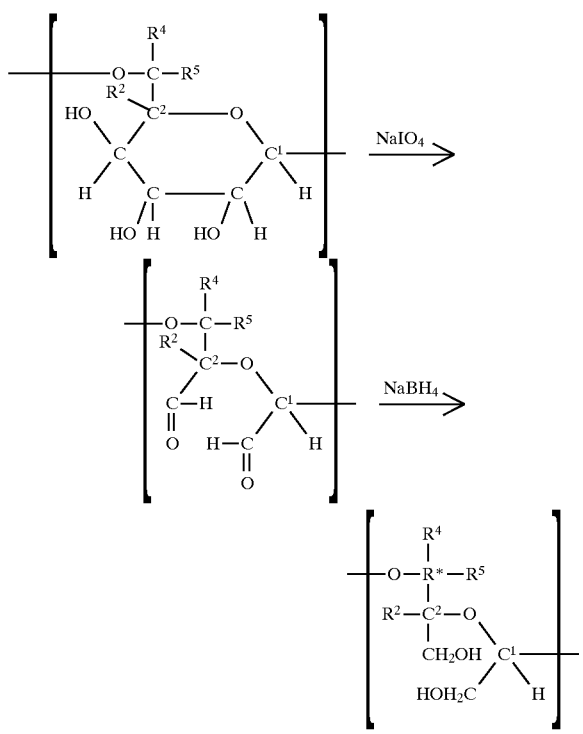

This process can be complicated by the formation of intra and interpolymer hemiacetals which can inhibit further polysaccharide oxidation. However, oxidative opening of the polysaccharide rings can be controlled by controlling the reaction conditions. In the present invention, it can be demonstrated that the polysaccharide oxidation, followed by reduction, causes synthesis of macromolecular biodegradable biocompatible polyacetals. The structure of the biodegradable biocompatible polyacetal obtained by the above mentioned method is dependent upon the precursor polysaccharide. Although it is generally not desirable, the polyacetal can contain intermittent irregularities throughout the polyacetal, such as incompletely oxidized additional groups or moieties in the main chain or in the side chains, as shown below:

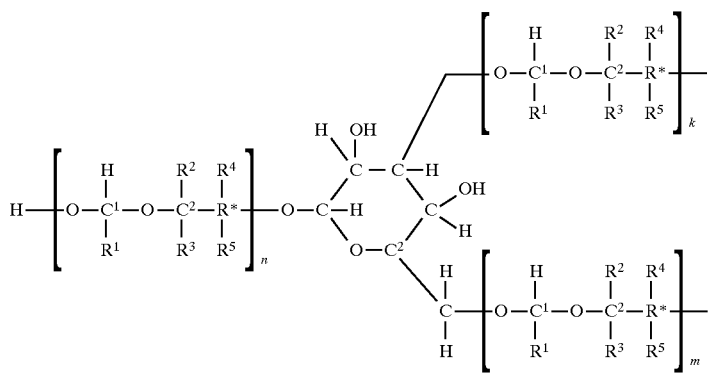

wherein k, m, and n are integers greater than or equal to one.

Since it is believed that oxidation does not affect configurations at the $C^1$ and $C^2$ positions, the aldehyde intermediate and the polyacetal retain the configuration of the parent polysaccharide and are formed in stereoregular isotactic forms.

The resultant biodegradable biocompatible polyacetal can be chemically modified by, for example, crosslinking the polyacetals to form a gel. The crosslink density of the biodegradable biocompatible polyacetal is generally determined by the number of reactive groups in the polyacetal and by the number of crosslinking molecules, and can be controlled by varying the ratio of polyacetal to the amount of crosslinker present.

For example, the biodegradable biocompatible polyacetal can be combined with a suitable aqueous base, such as sodium hydroxide, and crosslinked with epibromohydrin. Control of the amounts of epibromohydrin can determine the degree of crosslinking within the biodegradable biocompatible polyacetal gel. For example, biodegradable biocompatible polyacetals can be exposed to varying amounts of epibromohydrin for a period of about eight hours at a temperature about 80° C. to form crosslinked biodegradable biocompatible polyacetal gels which vary in crosslink density in relation to the amount of epibromohydrin utilized. The crosslinked biodegradable biocompatible polyacetal gel can further be reacted with a drug.

Treatment of the biodegradable biocompatible polyacetal with a suitable base, such as triethylamine in dimethylsulfoxide (DMSO), and an anhydride provides, for example, a derivatized polyacetal solution. Control of the amount of anhydride within the biodegradable biocompatible polyacetal can determine the degree of derivitization of the polyacetal in the solution.

In another embodiment of the present invention, treatment of poly-lysine labeled with DPTA (diethylenetriaminepentaacetic acid) with the biodegradable biocompatible polyacetal aldehyde, in water, for example, followed by subsequent reduction in water, provides a derivatized polyacetal solution.

In yet another embodiment of the present invention, oxidation of a dextran-stabilized iron oxide colloid with sodium periodate in water, followed by reduction with sodium borohydride in water, also forms a derivatized biodegradable biocompatible polyacetal solution.

Polyacetals of this invention can have a variety of functional groups. For example, aldehyde groups of an intermediate product of polysaccharide oxidation can be converted not only into alcohol groups, but also into amines, thioacetals, carboxylic acids, amides, esters, thioesters, etc.

Terminal groups of the polymers of this invention can differ from $R^1$, $R^2$, $R^3$, $R^4$, and $R^5$. Terminal groups can be created, for example, by selective modification of each reducing and non-reducing terminal unit of the precursor polysaccharide. One skilled in the art can utilize known chemical reactions to obtain desired products with varying terminal groups. For example, a hemiacetal group at the reduced end of the polyacetal can be readily and selectively transformed into a carboxylic acid group and further into a variety of other functional groups. A primary alcohol group at the non-reduced end can be selectively transformed into an aldehyde group and further into a variety of functional groups.

Alternatively, the biodegradable biocompatible polyacetals of the present invention can be formed by combining a cationic initiator with a precursor compound having the chemical structure:

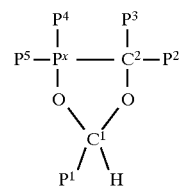

which forms a polymer having the chemical structure:

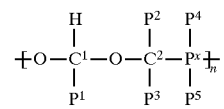

$P^1$ is a protected hydrophilic group which includes a carbon atom covalently attached to $C^1$. $P^1$ includes a carbon atom covalently attached to $C^2$. "n" is an integer. At least one of $P^1$, $P^2$, $P^3$, $P^4$ and $P^5$ is selected from hydrogen and protected hydrophilic groups suitable for conversion. $P^1$, $P^2$, $P^3$, $P^4$, and $P^5$ do not interfere with the cationic polymerization. Furthermore, $P^1$, $P^2$, $P^3$, $P^4$, and $P^5$ are suitable for conversion to hydrophilic groups as described above.

"Protected hydrophilic group," as that term is used herein, means a chemical group which will not interfere with decyclization of the precursor compound by the cationic initiator or subsequent polymerization, and which, upon additional treatment by a suitable agent, can be converted to a hydrophilic functional group. Examples of protected hydrophilic groups include esters, ethers, thioesters, thioethers, vinyl groups, haloalkyl groups, etc.

A method of treating mammals comprises administering to the mammal the biodegradable biocompatible polyacetal of this invention. For example, polyacetal can be administered in the form of soluble linear polymers, copolymers, colloids, particles, gels, solid items, fibers, films, etc. Biodegradable biocompatible polyacetals of this invention can be used as drug carriers and drug carrier components, in systems of controlled drug release, preparations for low-invasive surgical procedures, etc. Pharmaceutical formulations can be injectable, implantable, etc.

In one embodiment, a method for treating a mammal comprises administering to the mammal the biodegradable biocompatible polyacetal of the invention as a packing for a surgical wound from which a tumor or growth has been removed. The biodegradable biocompatible polyacetal packing will replace the tumor site during recovery and degrade and dissipate as the wound heals.

In another example, pharmaceutical excipients are incorporated in the biodegradable biocompatible polyacetal to form a biodegradable biocompatible mass of polyacetal in which the pharmaceutical excipient is entrapped. This can be achieved, e.g., by coupling the polyacetal with a pharmaceutical excipient. Alternatively, the pharmaceutical excipient can be entrapped by dissolution of the pharmaceutical excipient in the presence of the biodegradable biocompatible polyacetal during removal of a solvent. When these masses are implanted into a mammal, slow hydrolysis of the biodegradable biocompatible polyacetal mass occurs with continuous slow release of the excipient in the mammal at the location where its function is required.

The biodegradable biocompatible polyacetals of the present invention can be monitored in vivo by suitable diagnostic procedures. The diagnostic procedure can detect, for example, polyacetal disposition (e.g., distribution, localization, density, etc.) or the release of drugs, prodrugs, biologically active compounds or diagnostic labels from the biodegradable biocompatible polyacetals over a period of time. Such diagnostic procedures include nuclear magnetic resonance imaging (NMR), magnetic resonance imaging (MRI), ultrasound, radio waves, microwaves, X-ray, scintillography, positron emission tomography (PET), etc.

In one embodiment of the present invention, the biodegradable biocompatible polyacetal can be used as an interface component. The term "interface component" as used herein, means a component, such as a coating, of an object whereby adverse, or cytotoxic reactions, to the object are substantially prevented by the component. It should be understood that said object can be microscopic or macroscopic. Examples of microscopic objects include macromolecules, colloids, vesicles, liposomes, emulsions, gas bubbles, nanocrystals, etc. Examples of macroscopic objects include surfaces, such as surfaces of surgical equipment, test tubes, perfusion tubes, items contacting biological tissues, etc. It is believed that interface components can, for example, provide the object protection from direct interactions with cells and opsonins and, thus, to decrease the interactions of the object with the biological system.

Surfaces can be modified by the biodegradable biocompatible polyacetals of the present invention by, for example, conjugating functional groups of the biodegradable biocompatible polyacetals with functional groups present on the surface to be modified. For example, aldehyde groups of the biodegradable biocompatible polyacetal precursors can be linked with amino groups by employing reducing agents or isocyanides. Alternatively, carboxyl groups of the biodegradable biocompatible polyacetals can be conjugated with amino, hydroxy, sulphur-containing groups, etc. In another embodiment, a biodegradable biocompatible polyacetal of the invention which includes a suitable terminal group can be synthesized, such as a polyalcohol having a terminal carboxylic group. A polymer can be connected to a surface by reaction of the terminal group. Examples of suitable polymers include those formed, for example, by oxidation of a reducing-end acetal group into a carboxyl group, such as by using iodine or bromine. The remainder of the polysaccharide is then oxidized by employing a molar excess of a glycol-specific oxidizing agent to form an aldehyde. The aldehydes can be selectively modified by, for example, reduction into hydroxyl groups. The resulting polymer will generally have one terminal carboxyl group that can be used for one-point modification, such as by employing a carbodiimide.

In still another embodiment, a polysaccharide can be linked with a surface by reaction of a reducing-end aldehyde group of the polysaccharide, and subsequent oxidation and further conversion of the remainder of the polysaccharide.

It is to be understood that the biodegradable biocompatible polyacetals of this invention can be conjugated with macromolecules, such as enzymes, polypeptides, proteins, etc., by the methods described above for conjugating the biodegradable biocompatible polyacetals with functional groups present on a surface.

The biodegradable biocompatible polyacetals of the invention can also be conjugated with a compound that can physically attach to a surface via, for example, hydrophobic, van der Waals, and electrostatic interactions. For example, the biodegradable biocompatible polyacetal precursors can be conjugated with lipids, polyelectrolytes, proteins, antibodies, lectins, etc.

It is believed that interface components can prolong circulation of macromolecular and colloidal drug carriers. Therefore, biologically active compounds, diagnostic labels, etc., being incorporated in such carriers, can circulate throughout the body without stimulating an immunogenic response and without significant interactions with cell receptors and recognition proteins (opsonins). Further, interface components can be used to modify surfaces of implants, catheters, etc. In other embodiments of the present invention, biomedical preparations of the biodegradable biocompatible polyacetal can be made in various forms. Examples include implants, fibers, films, etc.

The invention will now be further and specifically described by the following examples. All parts and percentages are by weight unless otherwise stated.

EXEMPLIFICATION

Example 1: Formation of Aldehyde-Containing Polymer by Polysaccharide Oxidation

Dextran (MW=485 kDa), 22.5 g was dissolved in 500 mL water. Sodium periodate, 57 g, was dissolved in 200 mL of water and mixed with the dextran solution at 25° C. After 8 hours of incubation, the high-molecular components were extracted from the reaction mixture by flow dialysis, using a hollow fiber Amicon™ cartridge with a 10 kDa cutoff. The reaction mixture was concentrated to 200 mL, then a 10 fold volume of water (2 liters) was passed through. A forty mL aliquot of the reaction mixture was lyophilized to yield 1.81 g of product. The resultant polymer was slowly soluble in water at neutral and low pH and readily dissolved at pH>7 and remained soluble after pH adjustment to pH<7. Ten milligrams of the polymer were dissolved in deuterium oxide and a proton NMR was obtained.

Example 2: Formation of Polyalcohol by Reduction of Aldehyde-Containing Polymer

Sodium borohydride, 20 g, was dissolved in 20 mL water and mixed with 160 mL of 4.5% solution of the aldehyde containing polymer from Example 1. After 2 hours of incubation, the pH was adjusted to 6. Twenty minutes later, high molecular components were extracted by flow dialysis (as described in Example 1) and separated into two fractions using an Amicon cartridge with a 100 kDa cutoff. Both fractions were lyophilized. Yields: low molecular weight fractions: 2.4 g; high molecular weight fraction: 3.1 g. Ten milligrams of low molecular weight polymer were dissolved in 1 mL of deutero DMSO and proton NMR were obtained. FIG. 1 is a $^{13}C$ NMR of the polyacetal, dissolved in deuterium oxide which demonstrates carbons functionalized by alcohol functionality in the biodegradable biocompatible polyacetal.

Example 3: Formation of Crosslinked Polyalcohol Gels 760 milligrams of a high molecular weight fraction of polyalcohol polymer formed in Example 2 was dissolved in 10 mL of 5N sodium hydroxide. Eight mL of the solution was divided into equal portions into 4 test tubes, 2 mL in each. Epibromohydrin was added into each test tube in varying amounts: 20 microliters (tube #1), 50 microliters (tube #2), 100 microliters (tube #3), and 200 microliters (tube #4). The mixtures were carefully stirred to emulsify epibromohydrin with the polyalcohol. The reaction mixtures were incubated at 80° C. for 8 hours. After the incubation, gels were pulled out of the test tubes and washed in deionized water overnight.

The resultant gels differed in swelling volumes and rigidity. Gels swelled in proportion to the amount of bifunctional reagent used; i.e. gel #1 swelled approximately 10 fold whereas gel #4 did not swell. Rigidity of the gels increased with the increased amounts of bifunctional reagent. After initial swelling, volumes of the gels did not change over a 7 day period.

Example 4: Degradability of Crosslinked Polyalcohol Gels

Gels #1 (1 mL) and #3 (0.5 mL) of Example 3 were placed into 20 mL of 0.01M HCl and incubated at 25° C. under slow stirring. By the third hour of incubation, gel #1 was completely dissolved. Gel #3 was completely dissolved by day 4.

Example 5: Crosslinked Activated Gel

Ten milligrams of high molecular weight fraction polyalcohol from Example 2 was disclosed. Epibromohydrin, 50 microliters, was added and the mixture was stirred to emulsify epibromohydrin. The reaction mixture was incubated in a test tube at 60° C. for 1 hour. After the incubation, the gel was extracted from the test tube and washed in deionized water for 3 hours.

The gel was transferred into 2 mL of doxorubicine hydrochloride solution, 0.2 milligrams/mL, and the pH was adjusted to 8.5. After 14 hours of incubation, the gel was washed in water and then incubated in 0.001M HCl for 3 hours (pH adjusted to 3). After the incubation, the gel remained red, which indicated retention of significant amounts of doxorubicine. Analogous experiments with gels heated for 8 hours (Example 3) showed no doxorubicine retention.

Example 6: Polyalcohol-DTPA Derivative

Dry polyalcohol (Example 2), 50 milligrams, was dissolved in 0.2 mL DMSO and mixed with a solution of 2 milligrams of (DTPA) diethylenetriaminepentaacetic acid cycloanhydride in 0.05 mL DMSO. Ten microliters of triethylamine was added, and the reaction mixture was incubated for 1 hour. The resultant mixture was diluted with water (1 mL) and the polymer was separated by gel chromatography (Sephadex G 25/water) and lyophilized to yield 46 milligrams.

Example 7: Graft Copolymer of Polyalcohol and Poly-L-lysine- DTPA

A graft copolymer was produced via DTPA-labeled poly-L-lysine conjunction with aldehyde polymer followed by borohydride reduction. Two milligrams of poly-L-lysine (40 kDa hydrobromide, 85% modified with DTPA and labeled with Rhodamin X, 0.5% modification) was dissolved in 1 mL of water and mixed with 5 mL of 4.5% polyaldehyde solution (Example 1). After 10 minutes of incubation, 0.1 mL of 10 milligrams/mL sodium cyanoborohydride solution were added. One hour later, the reaction mixture was mixed with 1 mL of 50 milligrams/mL sodium borohydride. After 1 hour of incubation, the pH was adjusted to 6 and high molecular weight compounds were separated by gel-filtration (Sephadex G 25/water). The polymer fraction was separated into two fractions by diafiltration using Amicon™ YM-100 membrane. Rhodamin label and DTPA were found only in the high molecular fraction, indicating copolymer formation.

Example 8: Iron Oxide Colloid Stabilized by Polyalcohol

A dextran-stabilized iron oxide colloid (particle size 22±3 nm) was prepared as previously described (Papisov et al., J. Magnetism and Mag. Mater. 122 (1993), 383). A colloid solution in 10 mL of water (0.5 milligrams/mL by iron) was mixed with 1 gram dry sodium periodate and incubated for 1 hour at 25° C. Sodium borohydride, 1.47 g in 5 ml water was added, and the reaction mixture was incubated for 1 hr. Then pH was adjusted to 6.5. Twenty min. later, the colloid was precipitated with ethanol and resuspended in 10 ml water (3 tines). Ethanol was removed by vacuum evaporation and the colloid was dialysed against 0.9% NaCl. The resultant preparation was stable; particle size was practically unchanged (21±4 nm).

Example 9: Biokinetics of $^{111}$In Labeled Polyalcohol-DPTA Derivatives

Polyalcohol-DPTA derivative (example 6), 5 milligram was dissolved in 1 mL 0.2M sodium citrate buffer (pH=5.5) and mixed with a solution of $^{111}$ InCl, 52 $\mu$Ci. After a 5 minute incubation period, the In-labeled polymer was separated by gel chromatography (Sephadex G 25/0.9% NaCl) to yield 49 $\mu$Ci in 2 mL of eluate.

Figure 2:
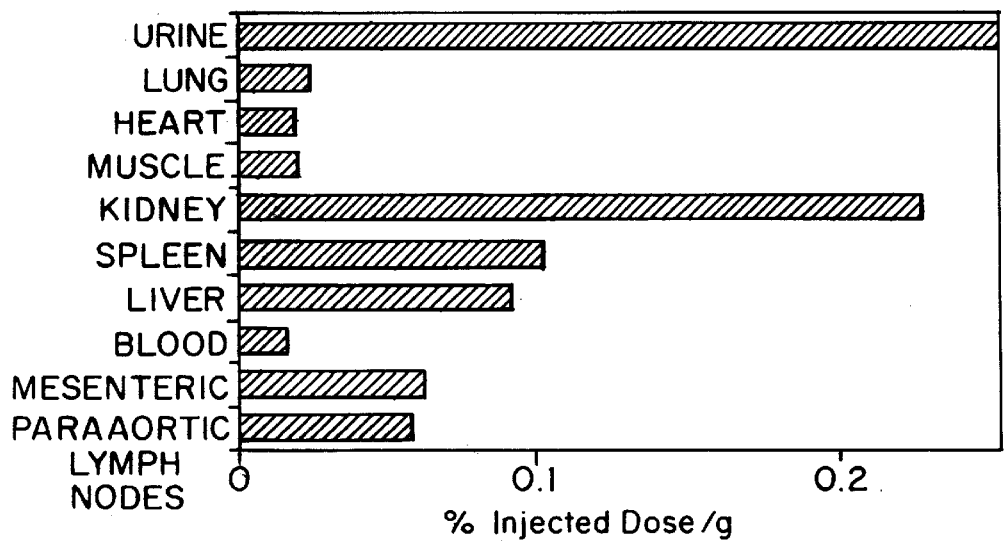
FIG. 2 a plot of the distribution of a radiolabelled biodegradable biocompatible polyacetal of the invention twenty hours after injection of the polyacetal into Sprague-Dawley CD rats.

Radiolabelled polymer was injected intravenously in two Sprague-Dawley CD rats (male, 200 and 300 g), 1.5 mg (15 $\mu$Ci) in each. Observation of radiolabel kinetics by dynamic scintigraphy demonstrated polymer circulation without accumulation in the reticuloendothelial system (and other tissues) with blood half-life ca. 2 hours. Study of radiolabel distribution 20 hours after injection confirmed low tissue uptake, as can be seen in FIG. 2.

Example 10: Crosslinked Polyaldehyde Gel

Polyaldehyde polymer (Example 1), 100 mg, was dissolved in 0.5 ml water. Ethylenediamide dihydrochloride, 5 mg, and sodium cyanobohydride, 5 mg, were dissolved in 0.02 ml water. Solutions were mixed. After 3 hr incubation, the resultant gel was washed with water and dried with ethanol.

Example 11: Polyacid of Polyaldehyde

Polyaldehyde polymer (Example 1), 20 mg, was dissolved in 1 ml water and, mixed with 5 ml 0.1M iodine solution in 0.1M KI. 1 ml of 1M NaOH was added by 5 μl aliquots. After 1 hr-incubation, polymer was separated using membrane filter with 10 kDa cutoff, purified by gel chromatography (Sephadex G-25/water) and lyophilized.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

I claim:

1. A biodegradable biocompatible polyacetal, comprising a compound which consists essentially of a chemical structure of:

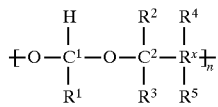

wherein $R^1$ is a biocompatible group and includes a carbon atom covalently attached to $C^1$, $R^x$ includes a carbon atom covalently attached to $C^2$, n is an integer, and wherein $R^2$, $R^3$, $R^4$ and $R^5$ are biocompatible groups and are each independently hydrogen or an organic moiety, and further provided that at least one of $R^1$, $R^2$, $R^3$, $R^4$ and $R^5$ is hydrophilic.

2. The biodegradable biocompatible polyacetal of claim 1 wherein the organic moiety is an alcohol.

3. The biodegradable biocompatible polyacetal of claim 1 wherein at least one of $R^1$, $R^2$, $R^3$, $R^4$ and $R^5$ is a methylol group.

4. The biodegradable biocompatible polyacetal of claim 1 wherein at least one of $R^1$, $R^2$, $R^3$, $R^4$ and $R^5$ is a drug.

5. The biodegradable biocompatible polyacetal of claim 4 wherein said drug includes an aldehyde group.

6. The biodegradable biocompatible polyacetal of claim 1 wherein at least one of $R^1$, $R^2$, $R^3$, $R^4$ and $R^5$ is a carboxyl group.

7. The biodegradable biocompatible polyacetal of claim 3 wherein $R^1$, $R^2$, $R^3$, $R^4$ and $R^5$ are methylol groups.

8. The biodegradable biocompatible polyacetal of claim 1 wherein $R^2$ is hydrogen.

9. The biodegradable biocompatible polyacetal of claim 1 wherein said polyacetal has a molecular weight of at least about 0.5 kDa.

10. The biodegradable biocompatible polyacetal of claim 1 wherein said polyacetal has a molecular weight between about 0.5 kDa and 500 kDa.

11. The biodegradable biocompatible polyacetal of claim 1 wherein said polyacetal has a molecular weight between about 1.0 and 100 kDa.

12. The biodegradable biocompatible polyacetal of claim 1 wherein at least one of $R^1$, $R^2$, $R^3$, $R^4$ and $R^5$ includes a biologically active compound.

13. The biodegradable biocompatible polyacetal of claim 1 wherein at least one of $R^1$, $R^2$, $R^3$, $R^4$ and $R^5$ includes a diagnostic label.

14. The biodegradable biocompatible polyacetal of claim 1 wherein said polyacetal is a stereoregular isotactic compound.

15. The biodegradable biocompatible polyacetal of claim 1 wherein said polyacetal is racemic.

16. A method for forming a biodegradable biocompatible polyacetal, comprising the steps of:

a) combining a molar excess of a glycol-specific oxidizing agent with a polysaccharide to form an aldehyde intermediate; and b) reacting the aldehyde intermediate to form said biodegradable biocompatible polyacetal polymer.

17. The method of claim 16 wherein the polysaccharide is a poly (1→6) hexose.

18. The method of claim 17 wherein the polysaccharide is dextran.

19. The method of claim 17 wherein the polysaccharide is cellulose.

20. The method of claim 17 wherein the polysaccharide is starch.

21. The method of claim 16 further including the step of reacting the biodegradable biocompatible polyacetal with a biologically active compound.

22. The method of claim 16 further including the step of reacting the biodegradable biocompatible polyacetal with a diagnostic label.

23. A method for forming a biodegradable biocompatible polyacetal, comprising the step of combining a cationic initiator with a compound having a chemical structure of:

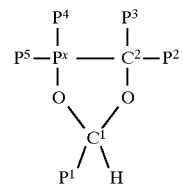

thereby forming a polymer having a chemical structure of:

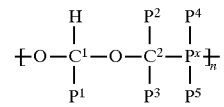

wherein $P^1$ is a protected hydrophilic group which includes a carbon atom covalently attached to $C^1$, and wherein at least one of $P^2$, $P^3$, $P^4$ and $P^5$ is selected from the group consisting of hydrogen and protected hydrophilic groups, n is an integer, and $P^x$ includes a carbon atom covalently attached to $C^2$.

24. The biodegradable biocompatible polyacetal of claim 1 wherein $R^1$ and $R^2$ are methylol and $R^3$, $R^4$ and $R^5$ are hydrogen.

25. The biodegradable biocompatible polyacetal of claim 1 wherein at least one of $R^1$, $R^2$, $R^3$, $R^4$ and $R^5$ includes a polypeptide.

26. The biodegradable biocompatible polyacetal of claim 25 wherein said polypeptide is poly-lysine.

27. The biodegradable biocompatible polyacetal of claim 1 wherein at least one of $R^1$, $R^2$, $R^3$, $R^4$ and $R^5$ includes a lipid.

28. The method of claim 16 further including the step of reacting the biodegradable biocompatible polyacetal with a polypeptide.

29. The method of claim 28 wherein said polypeptide is poly-lysine.

30. The method of claim 16 further including the step of reacting the biodegradable biocompatible polyacetal with a lipid.

* * * * *